(12) United States Patent
Coudray et al.

(10) Patent No.: US 6,407,557 B1
(45) Date of Patent: Jun. 18, 2002

(54) PROCESS FOR MEASURING THE ELECTRICAL RESISTANCE OF A RESISTIVE BODY FOR EXAMPLE FOR CHECKING THE CONFORMITY OF A LIQUID PRODUCT AND DEVICES FOR CARRYING OUT SUCH A PROCESS

(75) Inventors: Pascal Coudray, Melesse; Marie-Hélène Froger, Chateaugiron; Mickaël Lorgeoux; Christophe Truffaut, both of Rennes, all of (FR)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/383,625

(22) Filed: Aug. 26, 1999

(30) Foreign Application Priority Data

Aug. 27, 1998 (FR) .............................. 98 10774
Aug. 27, 1998 (FR) .............................. 98 10773

(51) Int. Cl.$^7$ .......................... G01R 27/08; G01R 27/26
(52) U.S. Cl. ...................... 324/708; 324/658; 324/660; 324/661; 324/662
(58) Field of Search ................. 324/708, 650, 324/71.1, 717, 658, 660, 661, 662; 347/7; 73/304 C

(56) References Cited

U.S. PATENT DOCUMENTS

| | | | | |
|---|---|---|---|---|
| 3,629,701 A | * | 12/1971 | Ichijo | 324/236 |
| 3,970,925 A | * | 7/1976 | Procter et al. | 324/649 |
| 4,120,370 A | * | 10/1978 | Bosson et al. | 177/185 |
| 4,238,726 A | * | 12/1980 | Ichijo | 324/650 |
| 4,259,632 A | * | 3/1981 | Ahtiainen | 324/664 |
| 4,427,938 A | * | 1/1984 | Prevot | 324/76.58 |
| 4,791,355 A | * | 12/1988 | Coulter et al. | 324/71.1 |
| 4,837,511 A | * | 6/1989 | Whittington | 324/236 |
| 4,875,940 A | * | 10/1989 | Radford | 127/2 |
| 4,922,182 A | * | 5/1990 | Cox | 324/682 |
| 5,072,186 A | * | 12/1991 | Trampert | 324/546 |
| 5,892,144 A | * | 4/1996 | Meller et al. | 73/64.42 |
| 5,521,515 A | | 5/1996 | Campbell | 324/674 |
| 5,736,938 A | * | 4/1998 | Ruthroff | 340/870.3 |
| 6,008,691 A | * | 12/1999 | Morita | 327/552 |

FOREIGN PATENT DOCUMENTS

| | | |
|---|---|---|
| DE | 3709665 | 10/1988 |
| DE | 4027657 | 11/1991 |
| EP | 28399 | 5/1981 |
| EP | 162580 | 11/1985 |
| EP | 856725 | 8/1998 |
| WO | 94/00912 | 1/1994 |

\* cited by examiner

Primary Examiner—N. Le
Assistant Examiner—Wasseem H. Hamdan
(74) Attorney, Agent, or Firm—Fitzpatrick, Cella, Harper & Scinto

(57) ABSTRACT

Measuring the electrical resistance of a resistive body, in particular a reservoir containing a printing product such as ink. According to the invention, the resistive body is used to define a capacitance arrangement formed from a capacitive branch which includes a capacitor electrically connected to the resistive body and this is incorporated in a resonant circuit that includes a variable capacitor. The resonant circuit is supplied with a fixed frequency, and as the capacitance of the variable capacitor is varied the peak of the signal is sought. The amplitude of the peak is representative of the resistance of the resistive body.

35 Claims, 8 Drawing Sheets

PROCESS FOR MEASURING THE ELECTRICAL RESISTANCE OF A RESISTIVE BODY FOR EXAMPLE FOR CHECKING THE CONFORMITY OF A LIQUID PRODUCT AND DEVICES FOR CARRYING OUT SUCH A PROCESS

FIELD OF THE INVENTION

The invention relates to a process for measuring the electrical resistance of a resistive body, possibly a resistive substance confined in a given volume, e.g. a conductive liquid contained in a reservoir, the resistance measurement being carried out without contact, i.e. in a non-destructive and non-intrusive manner. The invention also relates to a device for measuring the electrical resistance of a resistive body for carrying out the process and, by way of example, a device for measuring the quantity of a printing product contained in a reservoir, said printing product being resistive.

The invention also relates to a process for checking the conformity of a conductive liquid product contained in a reservoir. It also relates to a device for performing such a process. By way of example, the invention preferably relates to checking the conformity of a conductive printing product in a printer or other office machine incorporating such a printer.

As indicated above, the invention also relates in its operating principle to the measurement of the electrical resistance of a resistive body, because the information which is worked out by performing the process is directly related to the electrical resistance of an analysed resistive body. However, the invention can serve to measure and display any other magnitude, e.g. a quantity of product contained in a reservoir, if the variation in this magnitude is directly linked to that of the resistance by a known relationship.

DESCRIPTION OF THE PRIOR ART

The principle of a measurement of resistance without contact is already known in some applications. For example, U.S. Pat. No. 3,967,191 describes a process and a device for measurement of the electrical resistance of an internal film of a fluorescent lamp. The resistance of the film is measured by capacitive coupling. To achieve this, two metallic bands forming the plates of a capacitor are placed on the external wall of the lamp. One of the bands is connected to earth via a resistance, while the other is connected to a variable frequency generator via an inductance connected in series. Therefore, the whole constitutes a classic resonant RLC circuit, the resistance R being that of the internal film of the lamp. The frequency of the generator develops at relatively low frequencies, lower than or equal to 15 kHz. The inductance is selected and adjusted so that the resonance is produced during variation of the frequency in a given range. The amplitude of the resonance oscillations is measured to allow the resistance of the internal film of the lamp to be deduced.

Use of a variable frequency generator to detect the resonance frequency of an RLC circuit is a costly method and is a relatively slow process. In some systems, a measurement of this type must be made very rapidly and automatically without the knowledge of the user of the appliance, possibly to be able to prepare and display a message, i.e. to prevent operation of this appliance.

As for a printing machine one or more reservoirs of ink or pigmented product are to be found in an inkjet printer. In the following text the term "printing product" or even "ink" are used to refer to any liquid product which is appropriate for this use, including a colourless product known per se permitting better hold of the pigmented products on the paper. Only one reservoir is necessary if it is a black and white printer; if it is a colour printer, there are several reservoirs or compartments provided in the same cartridge which are filled with inks of different colours. Hence, in a high-quality colour printer, there may be up to seven cartridge reservoirs or compartments respectively enclosing inks of the following colours: black, dark cyan, light cyan, dark magenta, light magenta, dark yellow and light yellow. Therefore, it may be difficult for a person with little experience to easily replace or fill the reservoirs when necessary. While an error with black is rare, the risk of errors being made between two shades of the same colour is much more significant. Reversing light cyan and dark cyan reservoirs for example, can impair printing quality. The same applies for the other primary colours.

Moreover, the risks of errors differ according to the design of the printer. For example, in many printers an ejector head is closely associated with one reservoir. Sometimes, the print head is combined with the reservoir and is replaced at the same time as this, if it is a disposable reservoir.

If the system is based on one or more ink cartridges containing several reservoirs or compartments, as well as corresponding print head or heads, there is little risk of any handling error on the part of the user. However, this type of cartridge is expensive and its disposal may cause pollution. In fact, as soon as a reservoir or compartment is empty, the whole cartridge must be changed, which means that costly and polluting printing products are disposed of instead of being used. If the print head is separate from the reservoir or compartment which feeds it, an ink cartridge enclosing all the printing products allows errors to be avoided. Such a cartridge is more economical, but the pollution risks remain significant, since when a reservoir or compartment is empty, the whole cartridge must be changed.

Therefore, it may be preferred to use independent reservoirs, each reservoir possibly being associated with its own ink ejector head. In this case, an interchangeable reservoir only contains one single pigmented product. When one of these is empty, it is sufficient to replace only that one. However, the risks of error are much more significant.

There are also very significant risks of error when the printer comprises a number of reservoirs, which may be refilled by the user as and when required. In this case, there is the additional risk that a reservoir may be filled with an ink which is not appropriate, not only with respect to its exact colour, but also with respect to it quality, and use of such an ink may cause deterioration in the corresponding ink ejector head.

SUMMARY

In general, the process for measuring the electrical resistance in accordance with the invention is distinguished from the prior art in that it uses a resonant circuit comprising a variable capacitor forming means and in that the said resonant circuit is supplied with a fixed frequency. Advantageously, the variable capacitor forming means is a variable capacitance diode associated with an adjustable voltage generator, the advantage of this assembly being that it can be operated easily and quickly by varying the voltage applied to the diode, and the search for resonance and measurement of the corresponding peak amplitude can be operated in a very short time.

More precisely, the invention relates to a process for measuring the electrical resistance of a resistive body consisting of defining with said body a capacitance arrangement formed from a capacitive branch comprising at least one capacitor electrically connected to said resistive body and incorporating this capacitive section in a resonant circuit, characterised in that this resonant circuit additionally comprises a variable capacitor forming means, said resonant circuit being supplied with a fixed frequency, the capacitance of said capacitor being varied by measuring a signal delivered by said resonant circuit, the peak amplitude of this signal being measured and the value of this peak being representative of the resistance of said body.

As indicated above, the variable capacitor forming means preferably comprises a variable capacitance diode and an adjustable voltage generator connected to apply an inverse voltage to the terminals of said diode. The implementation of the process therefore consists simply of varying the capacitance of the capacitor by varying the voltage of the voltage generator according to a predetermined law. During this time, a peak amplitude detector connected to the resonant circuit allows said peak to be identified and its amplitude measured.

If the magnitude which has to be measured and checked is not, strictly speaking, the resistance of the resistive body, the process indicated above is supplemented by establishing a correlation between the values of the amplitude of said peak and predetermined values, written in memory, of a variation function of another variable dependent on said resistance.

For example, this other variable can be the quantity of a printing product contained in a reservoir provided that this printing product constitutes a resistive substance. In this case, at least one metal plate forming the capacitor is coupled to the reservoir of the printing product to form said capacitive branch. The process of measurement is performed and a value representative of the quantity of printing product remaining in the reservoir is deduced from the peak amplitude.

In this example, the capacitive branch can be considered as a series connection between the sought resistance and at least one capacitor formed by said metal plate acting as a plate of the capacitor, the insulating wall of the reservoir acting as dielectric, and the surface of the resistive body with respect to said metal plate. Preferably, the frequency supplying said resonant circuit is chosen in a range of frequencies for which it has been confirmed that the variation in capacitance was relatively independent of the quantity of ink contained in the reservoir. This is also the case in particular when the liquid printing product impregnates a spongy mass filling the reservoir.

The invention also relates to a device for measuring the electrical resistance of a resistive body, comprising a resonant circuit including a capacitive arrangement incorporating said resistive body to form a capacitive branch comprising at least one capacitor electrically connected to said resistive body, characterised in that the said resonant circuit additionally comprises a variable capacitor forming means, a fixed frequency oscillator, control means for variation of said variable capacitor, means for detecting a peak of a signal delivered by said resonant circuit, means of measuring the amplitude of this peak and means for preparing a signal representative of the said resistance of the said body.

By way of application, the invention also relates to a device for measuring the quantity of a printing product contained in a reservoir, said printing product being resistive, comprising a capacitive arrangement including at least one metal plate forming a capacitor plate, said reservoir and said printing product, and defining a capacitive branch, a resonant circuit incorporating the said capacitive branch, a fixed frequency oscillator, a variable capacitor forming means, control means for variation of said variable capacitor, means of detecting a peak of the signal delivered by said resonant circuit, means of measuring the amplitude of said peak and means for preparing a signal representative of a quantity of the printing product contained in said reservoir depending on the measured value of the peak amplitude.

The invention also proposes a process for checking the conformity of the ink used in such a context, and more generally checking the conformity of an electrically conductive liquid product.

In fact, it should be noted that the invention applies when the liquid product or products used have a certain resistivity. The invention consists in establishing a correlation between the resistivity of the product contained or reintroduced into the reservoir and its suitability for use with total safety in the device using such a conductive liquid product.

More precisely, the invention relates to a process for checking the conformity of a conductive liquid product contained in a reservoir, characterised in that it comprises forming a capacitive branch including the reservoir in question, and incorporating this capacitive branch in an oscillating circuit, applying an excitation signal to this oscillating circuit, picking up a resulting signal transmitted by said oscillating circuit, deducing from this resulting signal a value representative of the resistivity of the product contained in said reservoir, comparing this value to a prescribed interval of values, and at least producing a signal if the said value is outside the said interval.

In fact, it is established that in the field of printers using conductive inks of different colours, each ink has a specific resistivity. Therefore, a predetermined interval of resistivity can be attributed to it as a test of conformity. In practice, for a printer comprising several different inks, the intervals in question are not the same. Therefore, measurement of the resistivity of the replacement ink allows determination of whether this product is correct, so that the user can be made aware of the problem.

The system may possibly be supplemented by inhibitor means for the printing device, if a conformity check reveals use of an inadequate product.

Depending on the case, the process could be carried out after each change of reservoir or cartridge.

In order to obtain reliable measurements which may be easily used, the capacitive branch is incorporated in a resonant circuit and the resulting signal is picked up in correlation with the resonance conditions of the said resonant circuit. In other words, a correlation is established between the quality factor of the resonant circuit thus formed and the resistivity of the product inserted, from the electrical viewpoint, in said capacitive branch.

According to a preferred embodiment, the resonant circuit comprises a variable capacitor forming means, i.e. preferably a variable capacitor-type diode, the resonant circuit is supplied by a fixed frequency alternating signal, the capacitance of said variable capacitor is varied while measuring a said resulting signal delivered by said resonant circuit, the amplitude of the peak of this signal is measured and the value of this peak is representative of the resistivity of the said body. This type of measurement can be performed for a given reservoir each time this is replaced or filled. The correlation is effected simply after converting the amplitude of the peak into numerical data, consulting a look-up table recorded in a read-only memory of the control system to deduce therefrom the conformity of the ink contained in or introduced into the corresponding reservoir, via its resistivity.

The invention also relates to a device for checking the conformity of a conductive liquid product contained in a reservoir comprising a capacitive arrangement including the said reservoir to achieve a capacitive branch formed by at least one capacitor which is electrically connected to the conductive liquid product contained in said reservoir, characterised in that it comprises: means for incorporating the said capacitive branch into an oscillating circuit, means for exciting this oscillating circuit, means for picking up a resulting signal transmitted by the said oscillating circuit in response to said excitation signal, means for analysing this signal to deduce therefrom a value representative of the resistivity of the product contained in said reservoir, comparing means for determining whether said value is included in a prescribed interval of values, and means for producing a signal to emit at least one error message if the said value is outside the said corresponding interval.

By way of example, the invention also relates to any office machine comprising a device for checking conformity according to the above definition, in particular a printer or facsimile machine. The invention also relates to any microcomputer comprising at least one printing device fitted with a device for checking conformity according to the above definition.

In all cases, the office machine could comprise means for inhibiting a printing system including at least such a reservoir of printing product. These inhibitor means would be operated by a signal produced if an aforementioned.

The invention will be better understood and will be clearer in the light of the following description of a device for measuring the electrical resistance of a resistive body and of a device for measuring the quantity of printing product contained in a reservoir in an office machine comprising a printer, these two devices performing the process defined above, given only by way of example and with reference to the accompanying drawings, in which:

DETAILED DESCRIPTION OF THE INVENTION

Figure 1:
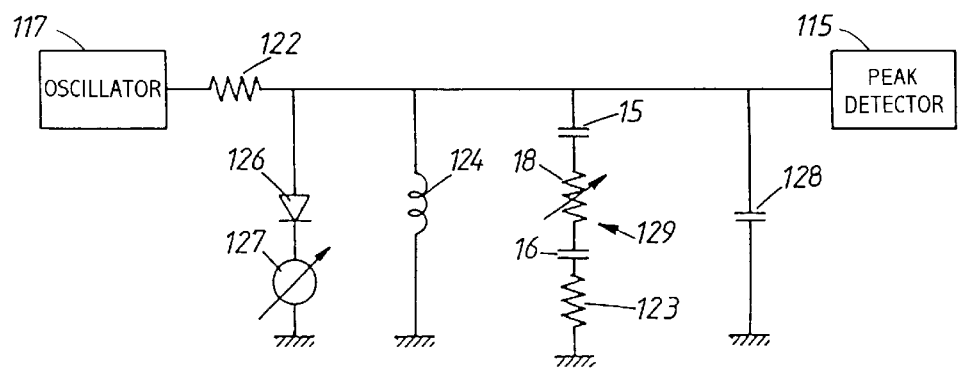
FIG. 1 is a schematic circuit diagram of a device for measuring the electrical resistance of a resistive body in accordance with the invention.
Figure 2A:
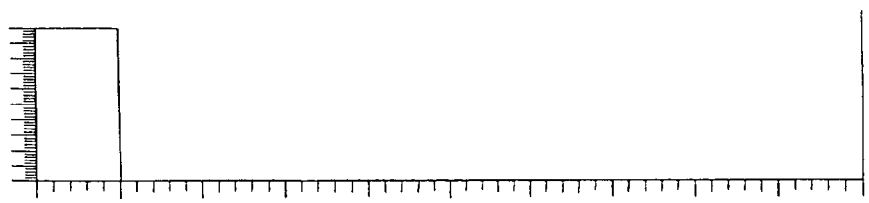
FIG. 2 is a graph showing the electrical signals applied to the device or produced by it for carrying out the process of the invention.
Figure 2B:
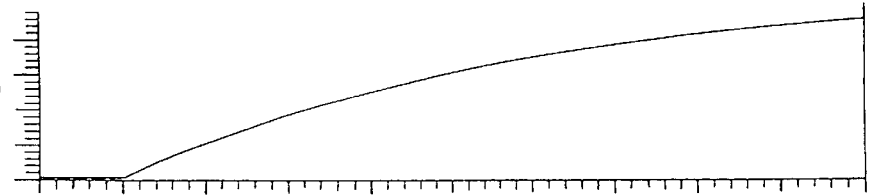
Figure 2C:
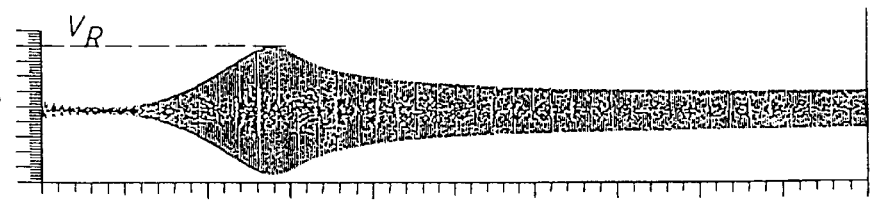
Figure 2D:
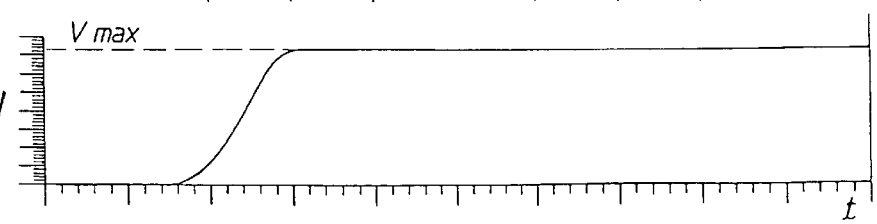

The device shown schematically in FIG. 1 comprises an oscillator 117 of fixed frequency, e.g. in the order of some MHz, preferably about 4 MHz, the output of which is connected to the input of a peak detector 115 by means of a resistance 122, here in the order of 100 k$\Omega$. Moreover, several circuit branches are connected in parallel between the link established between the resistance 122 and the detector 115 at one end and earth, at the other end. Clearly evident is a branch comprising a self-inductor 124, a branch comprising a variable capacitor diode 126 and, in series, an adjustable dc voltage generator 127, a branch formed by a capacitor 128 representing in fact the stray capacitances of a resonant circuit, and a "capacitive section" 129 formed by a series connection of a capacitor 15 connected to the resistance 122 and, at the input of the peak detector 115, of a variable resistance 18 representing a resistive body, typically a conductive product, of which it is desired to know the resistivity or resistance by performing the process, of a capacitor 16 and of a resistance 123 connected to earth. This resistance 123 is of low value, zero in certain cases. From an electrical viewpoint it adds to the resistance 18 (of a much more significant value) in the capacitive section 129. As clearly shown in FIG. 1, the resistance 18 is electrically connected between a plate of a capacitor 15 and a plate of a capacitor 16. Said capacitive section can in fact represent, from an electrical viewpoint, a capacitive arrangement associated with a reservoir for printing conductive product used in an inkjet type of printer (in association with a print head) as will be seen below. The voltage generator 127 is connected so as to apply an inverse voltage to the terminals of the diode 126 to vary its capacitance.

It is clearly shown that all the parallel branches form an RLC resonant circuit supplied by an oscillator. The frequency of this oscillator is calculated so that the circuit can resonate for a certain value of the capacitance of the diode 126 which constitutes, in association with the generator 127, a means for forming a variable and adjustable capacitor. An advantageous feature of the invention consists of supplying the resonant circuit with a fixed frequency to vary the capacitance of the capacitor, i.e. of the diode 126, while measuring a signal delivered by the resonant circuit by means of a peak detector 115. When the peak is detected, the amplitude of this is measured and the value of this peak is representative of the resistance 18 but also of the resistivity of the product which forms this resistance, under certain conditions which will be explained below.

It has been discovered that this assembly was that which exhibited the best possible precision (when resonance conditions are reached), whatever the value of capacitances entering the structure of this resonant circuit, in particular the value of the stray capacitance 128. Consequently, the amplitude of the detected signal on resonance has been revealed to be particularly representative of the value of the sought resistivity. This electric circuit can be formed since the resistance to be measured can be connected to the circuit by capacitive coupling. This coupling is represented here by the capacitors 15 and 16, which can be partly formed by the insulating walls of a printing product reservoir.

FIG. 2 shows the different signals permitting the invention to be performed.

Shown in a is a signal of a step voltage likely to be applied to the peak detector 115 for a return to zero thereof. With the initial conditions thus defined prior to measurement, the drop of the signal to the low state is utilised to actuate a progressive voltage variation of the generator 127, in this case in the form of an essentially linear ramp. This voltage variation is shown in b.

Shown in c is the signal present at the input of the detector 115 as a result of the variation in capacitance of the diode 126. In fact, the oscillator 117 generates a fixed frequency periodic signal, but the variation in inverse voltage applied to the diode 12 modifies its equivalent capacitance and as a result, the resonance frequency of the whole of the resonant circuit. When this resonance frequency corresponds to the frequency of the oscillator 117, a maximum amplitude VR is observed at the input of the detector 115. The peak detector is adapted to measure and record in memory this maximum amplitude. This recording to memory is shown in d. The peak value V max is representative of the resistance of said body. It also may be representative of the resistivity of a conductive product, i.e. the printing product contained in a reservoir.

As indicated above, a correlation can be established between the amplitude values of this peak and the predetermined values written to memory of a variation function of another variable dependent on the resistance 18. This other variable may be, for example, the quantity of a printing product contained in a reservoir of a printer.

Figure 3:
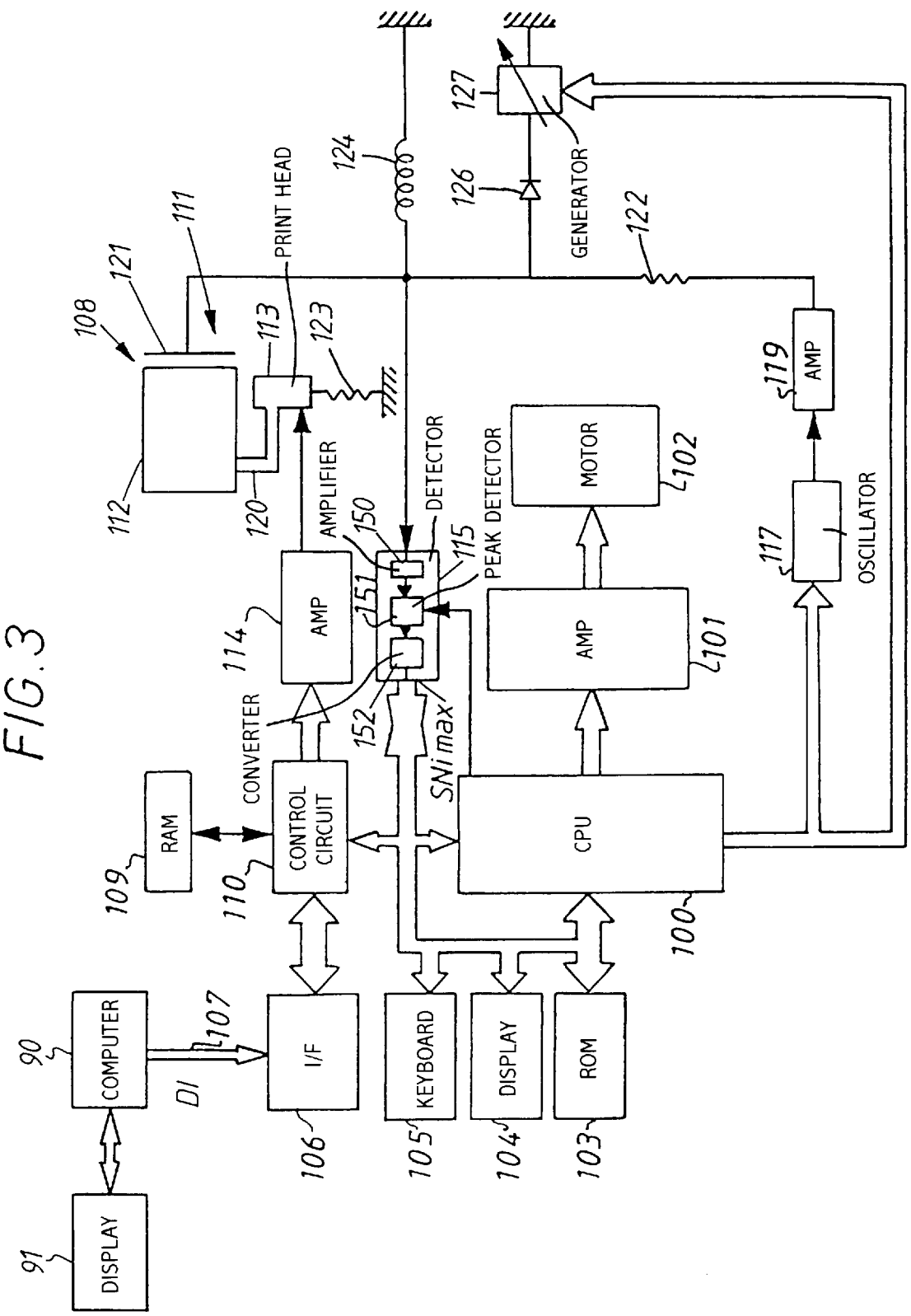
FIG. 3 is a schematic block diagram of a device for printing documents incorporating a measuring device according to the invention.
Figure 4:
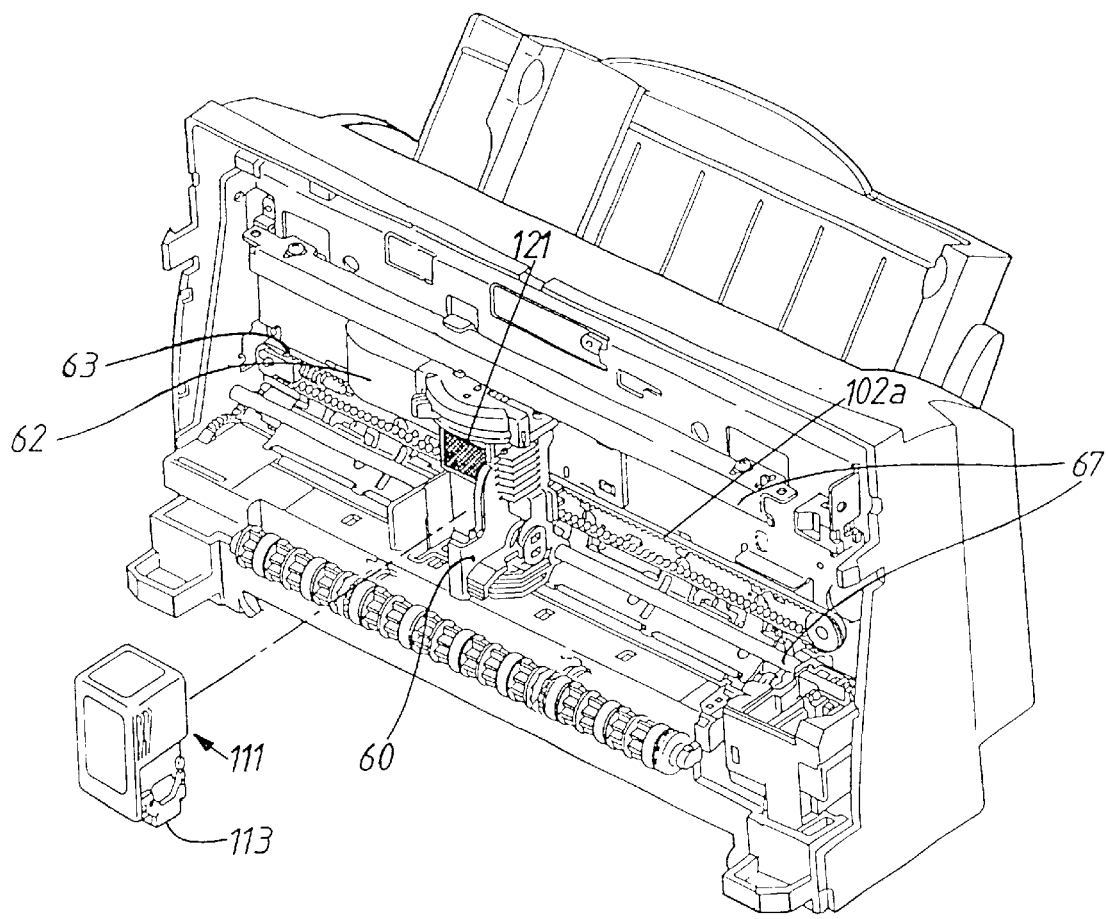
FIG. 4 is a partial perspective view of this printing device.
Figure 5:
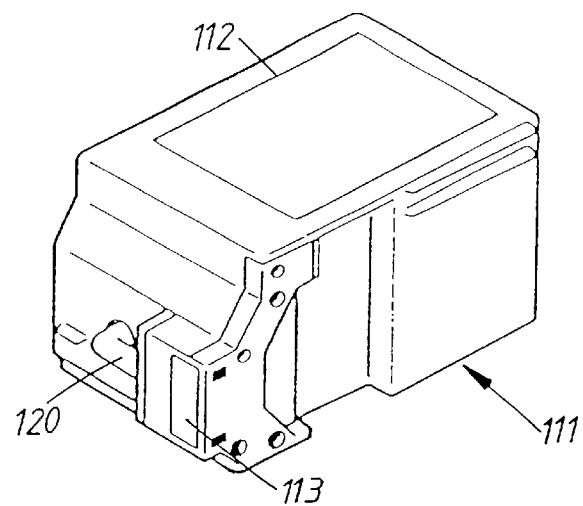
FIG. 5 is a detail view of a cartridge of printing product also including a printing head.

With particular reference to FIGS. 3 to 5, a printer is shown receiving the data to be printed Dl representing a text or an image, by means of an input-output port 107 connected to an interface circuit 106, which is itself connected to a control circuit for ink ejection 110 which drives a print head 113 via an amplification circuit 114. The printer can be connected, for example, via the input-output port 107 to a computer 90, which is itself connected to a display screen 91 or any other means of distributing data. The print head is connected to a reservoir 112 of printing product (ink or similar pigmented product). It should be noted that elements equivalent to those forming the circuit in FIG. 1 bear the same numerical references. The reservoir comprises a replaceable cartridge 111 also incorporating the print head 113 which, when it is in operation, is electrically connected to earth via the resistance 123. The reservoir 112 is connected to the print head 113 via a conduit 120. Such a cartridge can, for example, contain black ink for monochrome printing. In the case of colour printing, at least three reservoirs filled with printing products of different colours are provided which supply the corresponding printing heads respectively. The three classic colours are magenta, cyan and yellow.

The invention can also apply to detection of the level in the reservoir or each reservoir.

In the example, the cartridge 111 including the reservoir 112 and the print head 113 is mounted on a carriage 60 arranged for displacement along guide means 67 formed by parallel bars and rails. The carriage 60 is displaced in reciprocating motion along these guide means. It is driven by a motor 102 by means of a belt mechanism 102a well known to a person skilled in the art. The displacement path of the carriage 60, and thus of the printing heads 113, is parallel a printing line on a printing support such as a sheet of paper. This printing support is displaced perpendicularly to the path of displacement of the carriage by the printing mechanism, known per se.

The printer also comprises a main data processing circuit 100 connected to a read-only memory 103 and a read-write memory 109. The read-only memory 103 contains operating programs for the main processing circuit while the read-write memory 109, which is also connected to the ink ejection control circuit 110, stores on a temporary basis data received via the interface 106 as well as data prepared by the main processing circuit 100. The latter is connected to a display unit 104 on which it actuates the display of messages indicating the operation of the printer in general and, as will be seen below, in particular, of information on the quantity of printing product left in the reservoir.

The main processing circuit 100 is connected to a keyboard 105, via which the user can transmit operating commands to the printer. The processing circuit also actuates the motor 102 which drives the carriage by means of an amplification circuit 101. This motor is advantageously in the form of a stepper motor.

The printing device is equipped with a device for measuring the electrical resistance of the printing product, which constitutes a resistive body confined in the reservoir 112. However, it is not the resistance of the resistive body which one wishes to know but the quantity of the printing product still available in the reservoir. It has been determined that this quantity of ink was linked to the value of the resistance via a continuous function suitable for being used by putting in memory a look-up table in the read-only memory 103. This measuring device comprises a capacitive arrangement 108 including here the reservoir 112 and the print head 113 as well as a metal plate 121 carried by the carriage 60 and forming one of the plates of a capacitor of a capacitive branch 129 as illustrated in FIG. 1.

More precisely, it may be considered that, from the electrical viewpoint, this metal plate 121 forms the plate of capacitor 15 connected to the peak detector 115 providing the detection and the measurement means of the printer. These means, connected in cascade, are formed in particular by an amplifier 150, the input of which is connected to the plate 121 of a peak detector 151 driven by the main processing circuit 100, in particular for its return to zero in accordance with the graph in FIG. 2, and by an analog-to-digital converter 152, the output of which communicates with the main processing circuit 100. The latter is programmed to detect and write to memory a numerical value supplied by the converter 152 and representing a peak of the signal applied to the input of the amplifier 150 after reinitialisation of the peak detector 151.

The resonant circuit of FIG. 1 is arranged in the device in FIG. 3. This shows the fixed frequency oscillator 117 controlled by the main processing circuit 100, its output connected to the amplifier 119 which applies signals of constant frequency across the resistance 122 to the resonant circuit comprising the variable capacitance diode 126 polarised by the generator 127 which is itself controlled by the main circuit 100. The resistance 122 is also connected to the self-inductor 124 and to a capacitive arrangement including the plate 121, the reservoir 112 and its conductive printing product, the print head 113 connected to the reservoir via the conduit 120 and the low resistance 123 connected to earth. From the electric viewpoint, the assembly forms a capacitive branch 129 in keeping with that shown in FIG. 1. Hence, such a capacitor 15 is formed by the plate 121, the insulating wall of the reservoir 112, acting as dielectric, and the conductive printing product contained in the reservoir acting as the second plate of the capacitor 15. More precisely, it is the surface of the conductive product facing the plate 121 which defines the second plate of capacitor 15. As indicated above, the resistance 18 depends on the quantity of printing product contained in the reservoir and in the conduit 120. Additionally, the printing head 113 comprises a dielectric part and a conductive part which form the capacitor 16, this being connected to earth by the low resistance 123. As indicated above, stray capacitances of the resonant circuit accumulate in parallel at the input of the amplifier 150. They are not shown in FIG. 3, but are symbolised by the capacitor 128 in FIG. 1.

At the considered frequency, it is confirmed that for cartridges of the type described and illustrated in association with FIG. 5, the capacitances 15 and 16 practically do not vary in relation to the quantity of ink contained in the reservoir 112, but conversely the value of the resistance 18, representing electrically the conductive printing product, was representative of the quantity of printing product remaining in the reservoir. This resistance can in fact be measured with a relatively high degree of precision where resonance conditions of the circuit are in place, as has just been described. Use of a diode with variable capacitance is advantageous: it allows uncertainties in value to be compensated on other components of the circuit (typically in the order of 5% on the self inductances, capacitances and resistances) and on the mechanical configuration of the system, in particular the capacitive arrangement. In particular, the capacitors 15 and 16 can vary from one machine and/or reservoir to another. The diode allows normal operating conditions to be established in all circumstances, taking into account the frequency of the oscillator.

Figure 6:
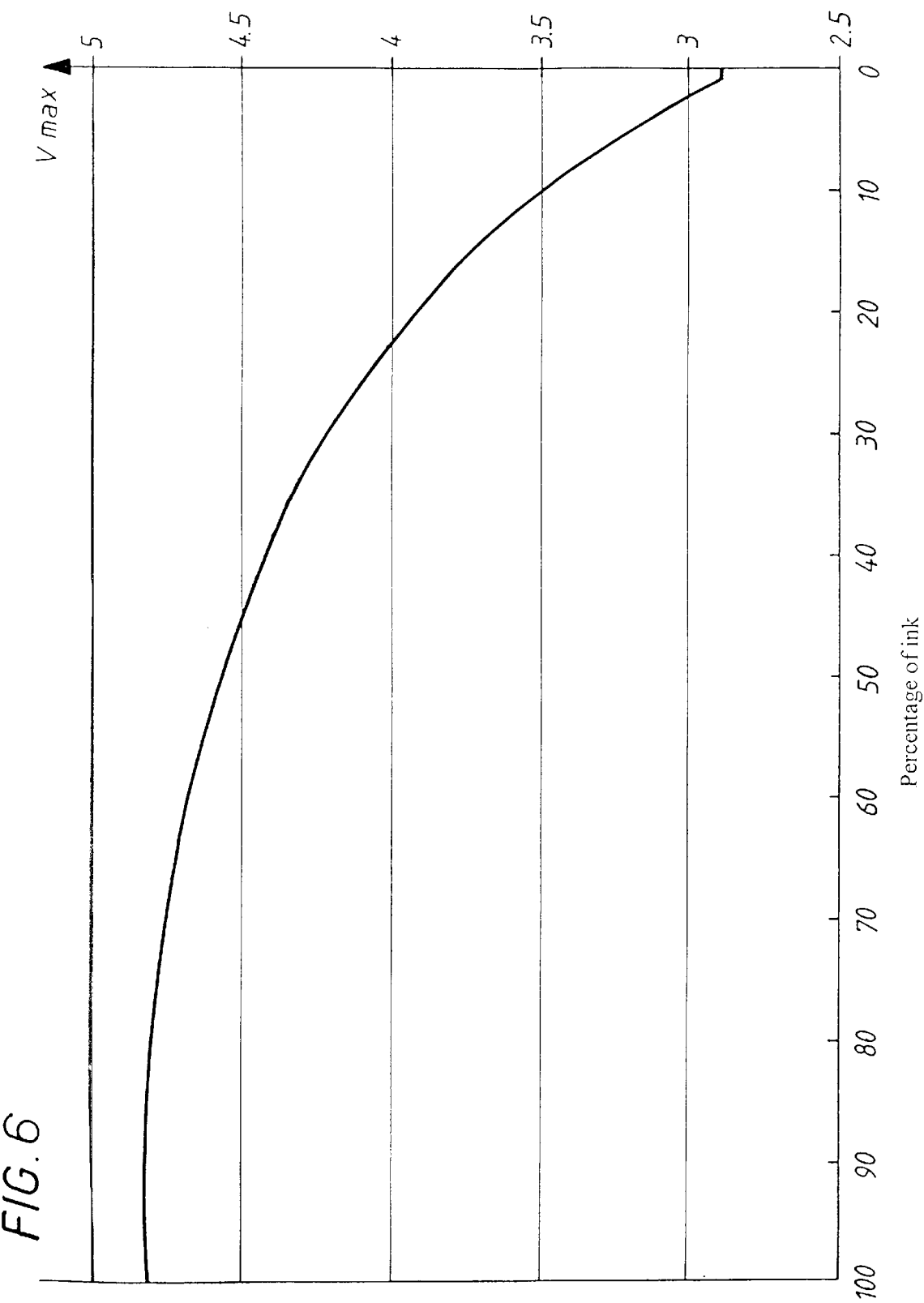
FIG. 6 is a graph illustrating the results obtained by the invention.

The curve in FIG. 6 illustrates the relation between the amplitude of the peak detected by the circuit 115 and the percentage of ink remaining in the reservoir 112. This curve is written to memory point by point in the read-only memory 103.

The reservoirs or cartridges of the conductive printing product for which the resistance varies greatly with the quantity of product are in particular those in which printing product impregnates a spongy mass located facing the plate 121 and filling at least part of the reservoir.

By way of example, different known print heads suitable to be used successfully for performing the invention are described in the published European patent applications EP 0 454 155, EP 0 641 654, EP 0 721 841 and EP 0 816 086.

Figure 7:
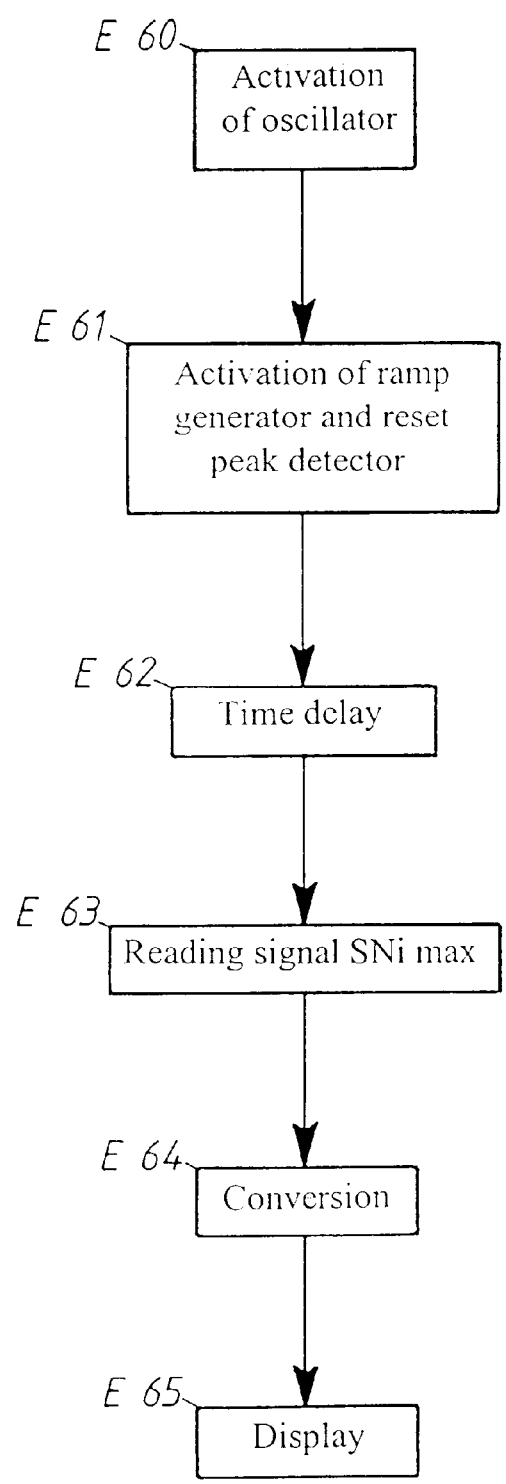
FIG. 7 is a flow chart of a program stored in a read-only memory in the printing device of FIG. 3 and performing the invention.

FIG. 7 shows an algorithm of a program written to memory in the read-only memory 103 of the printing device and worked out on each measurement of the quantity of printing product contained in the reservoir 112. This algorithm comprises six steps referenced E60 to E65 which are run through periodically, for example before printing a document. This algorithm allows determination of the quantity of ink remaining in the reservoir 115 at this instant.

In operation E60, the main processing circuit 100 actuates putting into service of the oscillator 60 which generates a square-wave signal of 0–5 volts amplitude, with a frequency of 4 MHz.

In step E61, the circuit 115 is driven to reinitialise the peak detector 151 and activate the generator 127 which works out a voltage ramp to achieve progressive variation of the capacitance of the diode 126.

In step E62, the circuit 100 actuates a waiting time of some hundreds of milliseconds to allow the ramp generator 127 to accomplish its predetermined variation.

In step E63, the main processing circuit 100 takes into account the numerical signal SNi max representing the maximum value of the voltage developed at the input of the amplifier 150 by the resonant circuit when this passes through the resonance conditions.

In E64 the main processing circuit 100 consults the read-only memory to find the information representative of the quantity of printing product corresponding to the peak value.

In state E65, the result is displayed, in particular on the display unit 104.

Numerous variants are possible. The conductive plate applied against the wall of the reservoir can be a metal plate carried by an integral support of the carriage, but also may be a plate which is fixed directly to the wall of the reservoir, i.e. metallisation thereof. Moreover, the other capacitor 16 can be formed not only by the print head, but also by another capacitor formed in the same manner as the capacitor 15, i.e. from another plate applied against another wall of the reservoir.

The invention also relates to any office machine characterised in that it comprises a device for determining the quantity of printing liquid remaining in at least one reservoir, in accordance with the above description and performing the process described.

The invention also relates to a printing device for documents incorporating such a measurement device. An office machine according to the invention can, for example, in essence comprise a printer, or a facsimile machine or even a microcomputer comprising or connecting to at least one device in question. Where operation is conducted in connection with a computer, this can be conventionally coupled to a printer enclosing the processing means according to the invention and to a display screen or any other means of distributing information. In this case, the information forming the result of the measurement can be returned to the computer 90 via the input-output port 107. The computer may therefore advantageously be programmed to operate the display of said information of the screen 91 or the means of distribution.

Figure 8:
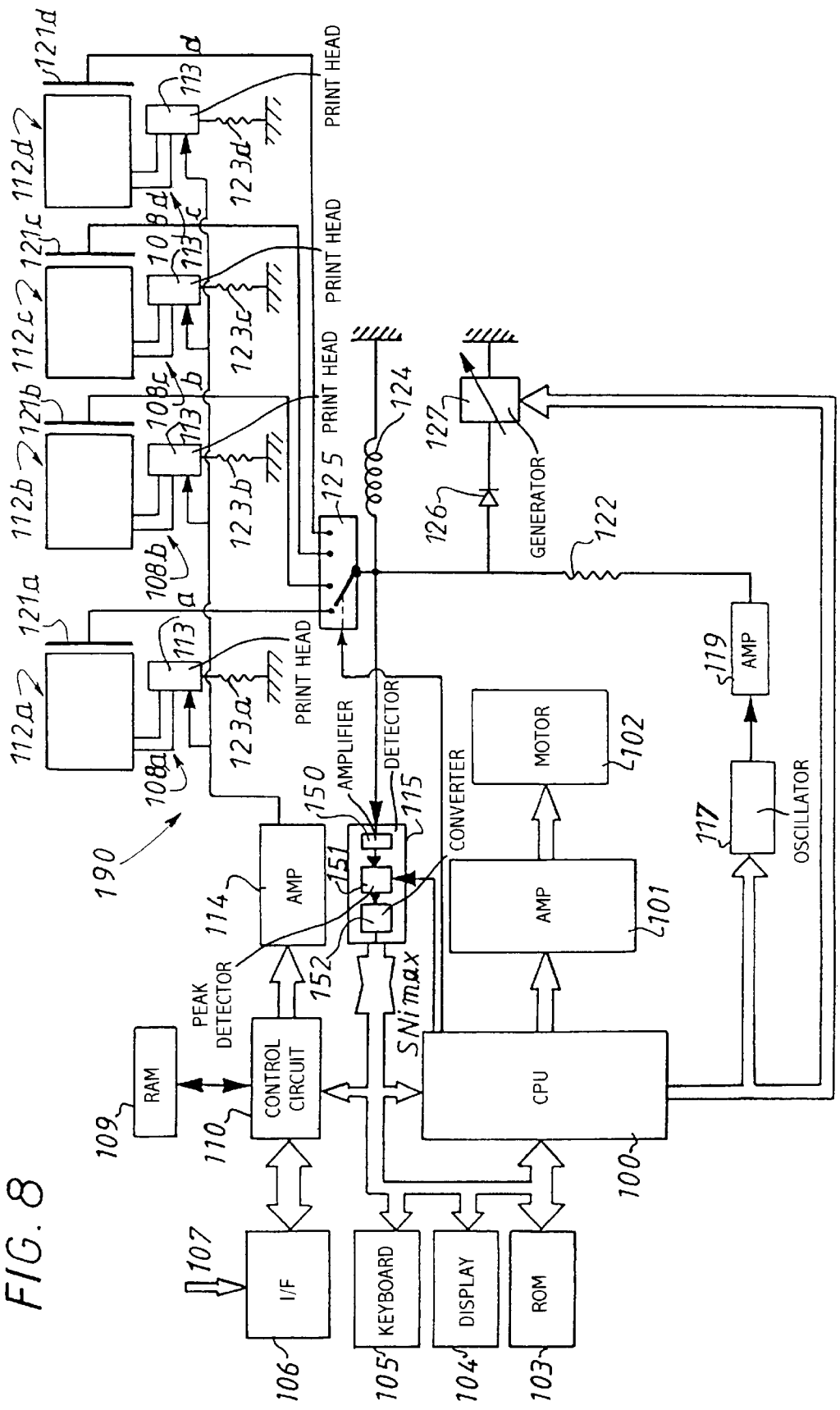
FIG. 8 is a block diagram of a device for printing documents incorporating a checking device according to the invention.
Figure 9:
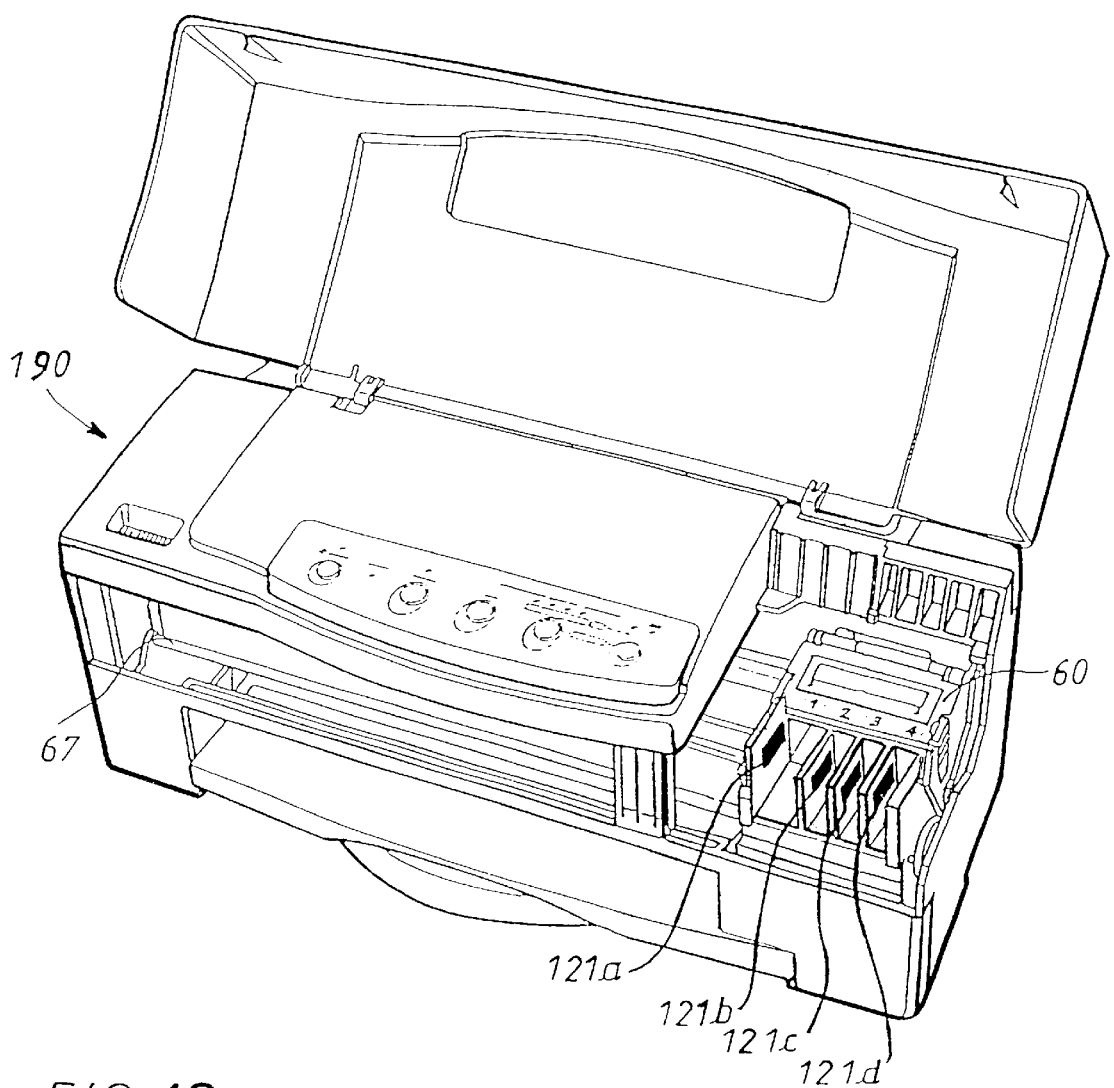
FIG. 9 is a perspective view of the printing device of FIG. 8.
Figure 10:
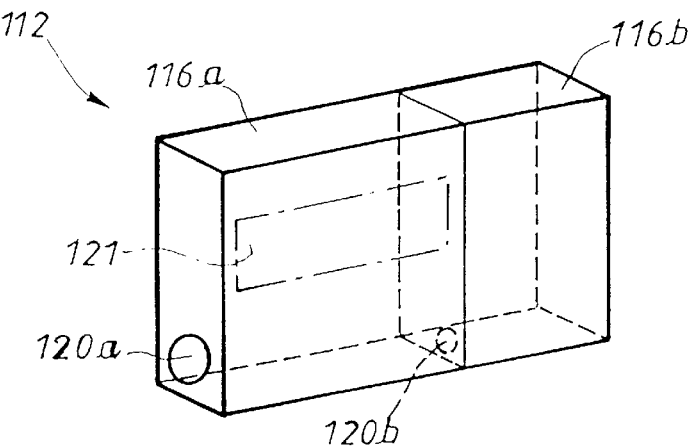
FIG. 10 is a detail view of a reservoir of printing product for the printing device of FIG. 9.

With particular reference to FIGS. 8 to 10, a colour printer 190 is shown. The parts of this printer similar to those if the printer of FIGS. 3–5 have the same reference numerals. The printer receives the data to be printed D1 representing a text or an image via a parallel input-output port 107 connected to an interface circuit 106, which is itself connected to a control circuit for ink ejection 110 which drives the print heads 113a, 113b, 113c, 113d via an amplification circuit 114. The print heads are respectively connected to ink reservoirs 112a, 112b, 112c, 112d. It should be noted that the elements equivalent to those forming the circuit in FIG. 1 bear the same reference numerals. According to the example, each reservoir is connected by a conduit to the corresponding print head 113a–113d which is electrically connected to earth via a corresponding low-value resistance 123a–123d. Reservoir 112a contains black ink for monochrome printing or printing in four colours. Reservoirs 112b, 112c, 112d contain inks of different colours for colour printing. The three classic colours are magenta, cyan and yellow.

In the example, reservoirs 112a–112d and printing heads 113a–113d are mounted on a carriage 60 arranged for displacement along guide means 67 formed by parallel bars and rails. The carriage 60 is displaced in reciprocating motion along these guide means. It is driven by a motor 102 by a belt mechanism well known to a person skilled in the art. The displacement path of the carriage 60, and thus of the printing heads 113a–113d, is parallel to a printing line on a printing support such as a sheet of paper. This printing support is displaced perpendicularly to the path of displacement of the carriage by the printing mechanism, known per se.

The printer also comprises a main data processing circuit 100 connected to a read-only memory 103 and a read-write memory 109. The read-only memory 103 contains operating programs for the main processing circuit while the read-write memory 109, which is also connected to the ink ejection control circuit 110, temporarily stores data received via the interface 106 as well as data produced by the main processing circuit 100.

The latter is connected to a display unit 104 on which it actuates the display of messages indicating the operation of the printer in general and, as will be seen below, in particular of information on the quantity of printing product left in the reservoir.

The main processing circuit 100 is connected to a keyboard 105, via which the user can transmit operating commands to the printer. The processing circuit also actuates the motor 102 which drives the carriage via an amplification circuit 101. This motor is advantageously in the form of a stepper motor.

A device for checking conformity of the ink comprises, for each reservoir, a capacitance arrangement 108a, 108b, 108c, 108d, respectively including here reservoir 112 and the corresponding printing head 113 as well as a metal plate 121a, 121b, 121c, 121d respectively carried by the carriage 60 and forming one of the plates of a capacitor of a capacitive branch 129, as illustrated in FIG. 1.

More precisely, it may be considered that, from the electrical viewpoint, this metal plate 121a–121d forms the plate of the capacitor 15 connected to the peak detector of the detection and the measurement means 115 of the printer. These means, connected in cascade, are formed in particular by an amplifier 150, the input of which is connected to the plate 121 of a peak detector 151 driven by the main processing circuit 100, in particular for its return to zero in accordance with the graph in FIG. 2, and by an analog-to-digital converter 152, the output of which communicates with the main processing circuit 100. The latter is programmed to detect and write to memory a numerical value supplied by the converter 152 and representing a peak of the signal applied to the input of the amplifier 150 after reinitialisation of the peak detector 151.

The resonant circuit of FIG. 1 is arranged in the device in FIG. 8. This shows the fixed frequency oscillator 117 controlled by the main processing circuit 100, its output connected to the amplifier 119 which applies signals of constant frequency across the resistance 122 to the resonant circuit comprising the variable capacitance diode 126 polarised by the generator 127 which is itself controlled by the main circuit 100. The resistance 122 is also connected to the self-inductor 124 and to a selected capacitive arrangement 108a–108d including the plates 121a–121d, the reservoir 112a–112d and its conductive printing product, the print head 113a–113d connected to the reservoir and the low-value resistance 123a–123d connected to earth. From the electric viewpoint, the assembly forms a capacitive branch 129 in keeping with that shown in FIG. 1. Hence, such a capacitor 15 is formed by the plate 121, the insulating wall of the reservoir 112, acting as dielectric, and the conductive printing product contained in the reservoir acting as a second plate of the capacitor 15. Additionally, the printing head 113 comprises a dielectric part and a conductive part which form the capacitor 16, this being connected to earth by the low-value resistance 123. As indicated above, stray capacitances of the resonant circuit accumulate in parallel at the input of the amplifier 150. They are not shown in FIG. 8, but are symbolised by the capacitor 128 in FIG. 1. The different plates 121a–121d are connected to the input of the detector 115 and to other components of the resonant circuit by a selector 125 driven by the circuit 100. This enables each capacitive section to be put into operation in succession.

FIG. 10 shows a schematic simplified view of an ink cartridge suitable for arrangement on the carriage 60. In this example, the cartridge 112 forming the reservoir comprises two compartments 116a, 116b. These two compartments are connected via an orifice 120b located on the lower portion of a dividing wall. Compartment 116a comprises a spongy mass impregnated with ink while compartment 116b contains the same ink, but does not contain the spongy mass. Consequently, upon use the product contained in compartment 116b allows the spongy mass in compartment 116a to be kept permanently impregnated. Compartment 116a is connected with the printing head 113a–113d via a conduit connected to the orifice 120a located in the lower portion of compartment 116a. It should be noted that the corresponding plates 121 (one of plates 121a–121d) in this case is located facing only compartment 116a, to the exclusion of compartment 116b. In these conditions, i.e. for this type of reservoir with two compartments, checking of conformity, i.e. measuring the resistivity, is relatively independent of the quantity of printing product contained in the reservoir. In other words, a measurement of resistivity permitting determinations of whether the printing product is in keeping with the manufacturer's stipulations could be performed at any instant so long as compartment 116b is not completely empty, i.e. so long as the spongy mass remains normally impregnated with printing product. However, there is obviously an interest in performing the process of checking conformity of the printing product after and immediately after the reservoir is replaced or filled. It is possible in this way to avoid use of an inappropriate product likely to damage the printing head or at least cause a deterioration in the printing quality. If the reservoir has only one compartment, i.e. does not have a compartment containing a spongy mass, the process of checking conformity will be most preferably performed immediately after the reservoir has been replaced or filled.

FIG. 10 shows as a dot-dash line the position of the plate 121 when the reservoir is in place on the carriage, said metal plate of course being supported by the dividing wall integral to this carriage (see FIG. 9).

In such measurement conditions, the resistance 18 is essentially independent of the quantity of product contained in the reservoir (either because the reservoir is full at the time of measurement, or because the spongy mass is normally impregnated), and in these conditions the value of the resistance 18 is only dependent on the shape and dimensions of the reservoir and on the resistivity of the product it contains. The value of this resistance can be evaluated with a relatively high degree of precision when the resonance conditions of the circuit just described are in place. More precisely, at resonance and in these specific conditions, the resistivity of the printing product is directly connected to the quality factor of the resonant circuit, i.e. to the amplitude of the signal measured at the input of the circuit 115. Consequently, performance of the process for checking conformity of the printing product contained in such a reservoir will consist of measuring the amplitude of the peak voltage (at the input of circuit 115) when the resonance conditions have been reached, converting this amplitude into numerical data SNi max and consulting a previously established look-up table recorded in the read-only memory 103 to deduce therefrom the conformity or lack of conformity of the product contained in the reservoir.

In practice, checking the conformity is performed as follows.

Preferably when one of the reservoirs 112a–112d has just been changed, the system places the selector 125 in a position such that the capacitive branch which it forms with the corresponding printing head is connected to the rest of the oscillating circuit formed by the self-inductor 124 and the variable 10 capacitance diode 126. The circuit 100 thus drives the generator 127 until a peak voltage is recorded at the input of the circuit 115. This peak corresponds to the resonance conditions. The value of this peak voltage, as has been seen, is representative of the resistivity of the product contained in the checked reservoir. The circuit 115 thus carries out the conversion into numerical data SNi max and is the circuit 100 is programmed to compare the value to a prescribed interval of values corresponding to the reservoir in question. If this value is not included in the interval, the circuit 100 produces a signal of lack of conformity indicating to the user that the printing product used is not appropriate and must be replaced. Of course, an interval of resistivity, i.e. an interval of voltage values in proximity to the resonance conditions, corresponds to each printing product contained in one of the reservoirs 112a–112d.

By way of example, the voltage value measured at the input of the circuit 115 as a function of the printing product can be as indicated below:

| | |
|---|---|
| black printing product: | 3.68 volts |
| cyan printing product: | 3.57 volts |
| magenta printing product: | 3.5 volts |
| yellow printing product: | 3.8 volts |

The corresponding value intervals are centred around these characteristic values with a chosen tolerance. Such values can be raised when the frequency of the oscillator 117 is relatively high, in the order of some MHz.

In the special case of a reservoir corresponding to FIG. 10, it has been found to be advantageous to lower the frequency of the oscillator 117 close to 100 kHz which means that the measurements are independent of the quantity of product present in compartment 116b so long as this is not completely empty, i.e. that the spongy mass of compartment 116 is normally impregnated.

Figure 11:
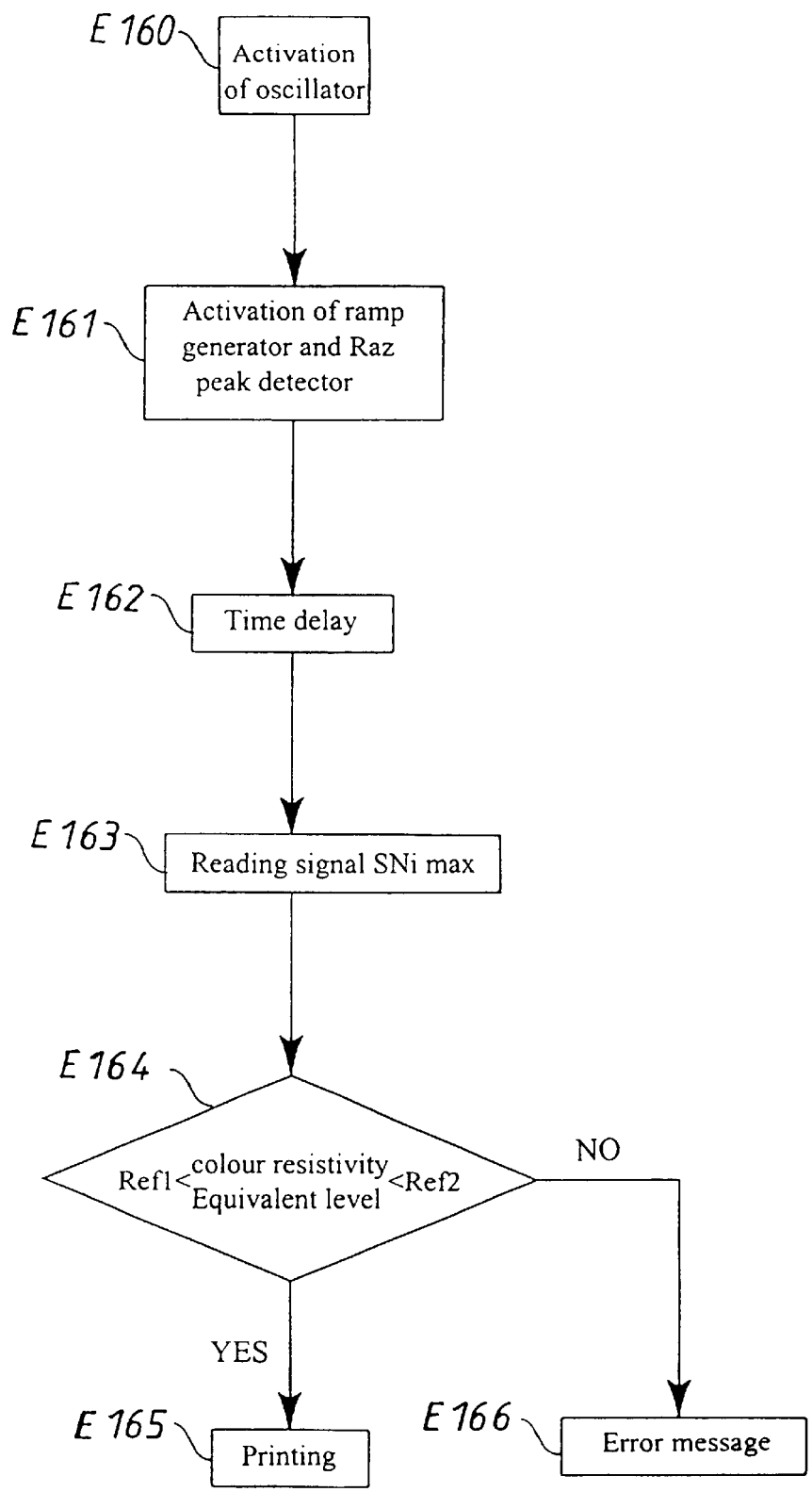
FIG. 11 is a flow chart of a program stored in a read-only memory in the printing device of FIG. 8 and performing the invention.

FIG. 11 shows a flow chart of a program stored in the read-only memory of the printing device and suitable for being carried out for checking conformity of each reservoir at a chosen instant. The algorithm comprises seven steps referenced E160 to E166. It can be performed for each reservoir upon a change of cartridge, or upon a change of one of the reservoirs or each time the printer is placed under voltage.

In operation E160, the central unit activates oscillator 117 which generates a square-wave signal of 0–5 volts amplitude and with a frequency equal, for example to two or some MHz.

In step E161, the peak detector 151 is returned to zero and the voltage generator 127 is actuated to produce a voltage ramp.

In step E162, the central unit actuates a waiting time of some hundreds of milliseconds to allow the ramp generator 127 to terminate its variation.

In step E163, the main processing circuit 100 actuates reading of the numerical signal SNi max representing the maximum value of the voltage applied to the input of the circuit 115 when the resonance conditions of the circuit correspond to the value of the frequency of the oscillator 117.

Step E164 is a test during which the main processing circuit 100 verifies whether the value SNi max is included in the corresponding interval [Ref 1–Ref 2] recorded in the read-only memory for the printing product in question. If the response is no, an error message is prepared in step E166. If the response is yes, the circuit 100 emits an authorization message to print or to actuate the selector 125 to pass on for checking of another reservoir. The circuit 100 may be programmed to comprise means for inhibiting the printing system if one of the aforesaid SNi max values is not included in a corresponding prescribed interval of values.

What is claimed is:

1. A method for measuring the electrical resistance of a resistive body comprising:

defining with said resistive body a capacitance arrangement formed from a capacitive branch comprising at least one capacitor electrically connected to said resistive body and incorporating said capacitance arrangement in a resonant circuit which additionally comprises a variable capacitor;

supplying said resonant circuit with a fixed frequency while varying the capacitance of said variable capacitor;

measuring a signal delivered by said resonant circuit during said supplying and varying step; and measuring the peak amplitude of said signal, wherein the value of said peak amplitude is taken as representative of the resistance of said resistive body.

2. A method according to claim 1, wherein said variable capacitor further comprises a variable capacitance diode and an adjustable voltage generator connected to apply an inverse voltage to the terminals of said diode, the capacitance of said variable capacitor being varied by varying the voltage of said adjustable voltage generator according to a predetermined law.

3. A method according to claim 1, wherein a correlation is established between potential values of the peak amplitudes and predetermined values written in memory of a variation function of another variable dependent on said resistance.

4. A method according to claim 3, further comprising coupling at least one metal plate forming the capacitor to a reservoir of said resistive body to form said capacitive branch, varying the capacitance of said variable capacitor to search for said peak amplitude, and measuring the value of the peak amplitude and deducing a value which is representative of the level of printing product contained in the reservoir.

5. A method according to claim 4, further comprising measuring the peak amplitude, converting the peak amplitude into numerical data, and consulting a pre-established look-up table to deduce therefrom the conformity of the printing product contained in said reservoir.

6. Device for measuring the electrical resistance of a resistive body, comprising:

a resonant circuit including a capacitive arrangement incorporating said resistive body and comprising at least one capacitor electrically connected to said resistive body to form a capacitive branch, said resonant circuit additionally comprising a variable capacitor;

an oscillator connected to supply a fixed frequency to said resonant circuit;

control means for varying said variable capacitor;

means coupled to said resonant circuit for detecting a peak amplitude of a signal delivered by said resonant circuit; and means for measuring the value of said peak amplitude and for generating therefrom a signal representative of the resistance of the resistive body.

7. Device according to claim 6, wherein said variable capacitor comprises a variable capacitance diode and an adjustable voltage generator connected to apply an inverse voltage to the terminals of said diode.

8. Device according to claim 6, wherein said resonant circuit comprises a self-inductance.

9. Device for measuring the quantity of a printing product contained in a reservoir, said printing product being resistive, comprising:

a capacitive arrangement including at least one metal plate forming a capacitor plate and further including said reservoir and said printing product, said capacitive arrangement defining a capacitive branch;

a resonant circuit incorporating said capacitive branch and a variable capacitor;

an oscillator connected to supply a fixed frequency to said resonant circuit;

control means for varying capacitance of said variable capacitor;

means coupled to said resonant circuit for detecting a peak amplitude of a signal delivered by said resonant circuit; and means for measuring the value of said peak amplitude and for generating a signal representative of a quantity of the printing product contained in said reservoir depending on the measured value of the peak amplitude.

10. Device according to claim 9, wherein said variable capacitor comprises a variable capacitance diode and an adjustable voltage generator connected to apply an inverse voltage to the terminals of said diode.

11. Device according to claim 9, wherein said resonant circuit comprises a self-inductance.

12. Device according to claim 9, further comprising display means for displaying said signal representative of the quantity of the printing product.

13. Office machine, including a device for measuring the electrical resistance of a resistive body, comprising:

a resonant circuit including a capacitive arrangement incorporating said resistive body and at least one capacitor electrically connected to said resistive body to form a capacitive branch, said resonant circuit additionally comprising a variable capacitor;

an oscillator connected to supply a fixed frequency to said resonant circuit;

control means for varying said variable capacitor, means coupled to said resonant circuit for detecting a peak amplitude of a signal delivered by said resonant circuit; and means for measuring the value of said peak amplitude and for generating therefrom a signal representative of the resistance of the resistive body.

14. Office machine according to claim 13, which comprises a printer.

15. Office machine according to claim 13, which comprises a facsimile machine.

16. Data processing assembly, including at least one printing device fitted with a device for measuring the quantity of a printing product contained in a reservoir, said printing product being resistive, comprising:

a capacitive arrangement including at least one metal plate forming a capacitor plate and further including said reservoir and said printing product, said capacitive arrangement defining a capacitive branch;

a resonant circuit incorporating said capacitive branch and a variable capacitor;

an oscillator connected to supply a fixed frequency to said resonant circuit;

control means for varying capacitance of said variable capacitor;

means coupled to said resonant circuit for detecting a peak amplitude of a signal delivered by said resonant circuit; and means for measuring the value of said peak amplitude and for generating a signal representative of a quantity of the printing product contained in said reservoir depending on the measured value of the peak amplitude.

17. Data processing assembly according to claim 16, further comprising a computer and a display screen under the control of said computer to display information representative of said signal.

18. A method for checking the conformity of a conductive liquid product contained in a reservoir, comprising:

forming a capacitive branch including the reservoir and connecting said capacitive branch into an oscillating circuit;

applying an excitation signal to said oscillating circuit;

detecting a resulting signal transmitted by said oscillating circuit and resulting from the excitation signal applied in said applying step;

calculating from said resulting signal a value representative of resistivity of the liquid product contained in said reservoir; and comparing said value to a prescribed interval of values, and producing a conformity signal at least in a case where said value is outside the interval of values.

19. A method according to claim 18, wherein said capacitive branch is incorporated in a resonant circuit and said resulting signal is picked up in correlation with resonance conditions of said resonant circuit.

20. A method according to claim 19, wherein a correlation is established between said value representative of resistivity and the quality factor of said resonant circuit.

21. A method according to claim 19, wherein said resonant circuit further comprises a variable capacitor, and further comprising the steps of supplying said resonant circuit with a fixed frequency alternating signal, varying the capacitance of said variable capacitor while measuring said resulting signal as delivered by said resonant circuit, and measuring the value of the peak amplitude of said resulting signal, wherein the value of the peak amplitude is taken as representative of the resistivity of said liquid product.

22. A method according to claim 21, further comprising converting the measured value of the peak amplitude into numerical data and consulting a pre-established look-up table to deduce therefrom the conformity of the liquid product contained in said reservoir.

23. A method according to claim 18, wherein the method is performed for a given reservoir subsequent to said reservoir being replaced or filled.

24. A method according to claim 23, wherein the method is performed in a printer for each reservoir or cartridge compartment thereof containing a given ink having a specific predetermined resistivity, the performance of the method being actuated subsequent to such a reservoir or cartridge compartment being replaced or filled.

25. Device for checking the conformity of a conductive liquid product contained in a reservoir, comprising:
- a capacitive arrangement including a capacitive branch formed from at least said reservoir and at least one capacitor which is electrically connected to the conductive liquid product contained in the said reservoir,
- an oscillating circuit;
- means for integrating said capacitive branch into said oscillating circuit;
- means for applying an excitation signal to said oscillating circuit;
- means for detecting a resulting signal transmitted by said oscillating circuit in response to said excitation signal;
- means for analyzing the resulting signal to deduce therefrom a value representative of resistivity of the liquid product contained in said reservoir;
- comparing means for determining whether said value is included in a prescribed interval of values; and
- means for producing a signal to emit at least one message in a case where said value is outside said prescribed interval of values.

26. Device according to claim 25, wherein said oscillating circuit is comprised of a resonant circuit which includes means for detecting a peak of said resulting signal delivered by said resonant circuit and means for producing a signal representing the resistivity of said liquid product.

27. Device according to claim 26, wherein said resonant circuit is supplied at a fixed frequency and comprises a variable capacitor and a variation control means for varying capacitance of said variable capacitor.

28. Device according to claim 27, wherein said variable capacitor comprises a variable capacitance diode and an adjustable voltage generator connected to apply an inverse voltage to the terminals of the said diode.

29. Device according to claim 27, wherein said resonant circuit comprises a self-inductor.

30. Device according to claim 25, wherein said liquid product is a resistive printing product, and wherein the capacitance arrangement comprises at least one conductor plate forming the plate of the capacitor which is applied against a wall of a reservoir made of an insulating material enclosing said printing product.

31. Device according to claim 30, further comprising plural capacitance branches each associated with corresponding ones of plural different reservoirs containing printing products with different resistivity, wherein said means for integrating said capacitance branch comprises selection means allowing a selected capacitance section including a given reservoir to be connected to the rest of the resonant circuit.

32. Device according to claim 30, further comprising inhibitor means for inhibiting a printing system including at least one such reservoir, said inhibitor means being actuated if an aforesaid value is not included in a corresponding prescribed interval of values.

33. Office machine, comprising a device for checking the conformity of a conductive liquid product contained in a reservoir, comprising:
- a capacitive arrangement including a capacitive branch formed from at least said reservoir and at least one capacitor which is electrically connected to the conductive liquid product contained in the said reservoir;
- an oscillating circuit;
- means for integrating said capacitive branch into said oscillating circuit;
- means for applying an excitation signal to said oscillating circuit;
- means for detecting a resulting signal transmitted by said oscillating circuit in response to said excitation signal;
- means for analyzing the resulting signal to deduce therefrom a value representative of resistivity of the liquid product contained in said reservoir;
- comparing means for determining whether said value is included in a prescribed interval of values; and
- means for producing a signal to emit at least one message in a case where said value is outside said prescribed interval of values.

34. Office machine according to claim 33, which comprises a printer.

35. Office machine according to claim 33, which comprises a facsimile machine.

* * * * *